(12) United States Patent
Borosic

(10) Patent No.: US 6,925,920 B1
(45) Date of Patent: Aug. 9, 2005

(54) KNIFE HOLDER AND KNIFE FOR A MICROTOME

(75) Inventor: Drago Borosic, Eppelheim (DE)

(73) Assignee: Microm International GmbH, Walldorf (DE)

( * ) Notice: Subject to any disclaimer, the term of this patent is extended or adjusted under 35 U.S.C. 154(b) by 0 days.

(21) Appl. No.: 09/549,130

(22) Filed: Apr. 13, 2000

Related U.S. Application Data

(63) Continuation-in-part of application No. PCT/EP98/06437, filed on Oct. 12, 1998.

(30) Foreign Application Priority Data

Oct. 13, 1997 (DE) ................ 197 44 983

(51) Int. Cl.[7] ............... G01N 1/06; B26D 1/02; B26D 7/26
(52) U.S. Cl. ............... 83/522.15; 83/699.51; 83/856; 83/857; 83/858; 83/915.5; 83/955; 30/339; 30/351; 30/353
(58) Field of Search .......... 83/703, 704, 705, 83/856, 857, 858, 915.5, 932, 707, 437.1, 83/437.2, 699.31, 699.51, 713, 714, 717, 83/955, 522.15; 30/41.7, 279.6, 346.52, 346.57, 30/329, 339, 346.61, 351, 353, 287

(56) References Cited

U.S. PATENT DOCUMENTS

| 847,308 | A | * | 3/1907 | Baker et al. | ........... 30/41.7 X |
| 3,611,875 | A | * | 10/1971 | Wistedt et al. | ......... 83/915.5 X |
| 3,648,365 | A | | 3/1972 | Iten et al. | ................ 30/40 |
| 4,241,500 | A | * | 12/1980 | Iten | ................ 30/40 |
| 4,700,600 | A | | 10/1987 | Pickett | ................ 83/165 |

FOREIGN PATENT DOCUMENTS

FR 2 549 098 A1 1/1985

\* cited by examiner

*Primary Examiner*—Clark F. Dexter

(57) ABSTRACT

The invention relates to a knife holder for a microtome having a knife receiver for fixing and positioning a knife and a knife for the knife holder. The knife holder is ergonomic, the operation is made easier and safer, and the knife does not need to be changed as often. To this end, the knife receiver is constructed to accommodate a disk-shaped knife. The knife is given the shape of a regular polygon, whereby the edges are cutters. The knife receiver has an axle on which the knife can rotate such that the cutters can be positioned for cutting an object.

11 Claims, 1 Drawing Sheet

KNIFE HOLDER AND KNIFE FOR A MICROTOME

CROSS-REFERENCES TO RELATED APPLICATIONS

This application is a continuation-in-part of PCT/EP98/06437 filed Oct. 12, 1998.

STATEMENT REGARDING FEDERALLY SPONSORED RESEARCH OR DEVELOPMENT

Not Applicable.
REFERENCE TO A MICROFICHE APPENDIX
Not Applicable.

BACKGROUND OF THE INVENTION

The invention relates to a knife holder for a microtome, with a knife receiver for arresting and positioning a knife, and also a knife for this knife holder.

Microtomes find application in histology and are used for the production of tissue sections, which are then investigated under the microscope. For the production of the tissue sections, the microtome passes the object to be sectioned past a stationary knife, which must be very sharp and which is therefore held by a knife holder as an interchangeable blade.

DISCUSSION OF RELEVANT ART

A knife holder of the above-mentioned kind is known from the brochure "2040 AUTOCUT" of the Reichert-Jung Corapany; a knife constructed as an elongate blade is clamped in it. In order not to have to constantly change the knife, it is constructed with a length such that it can be displaced with respect to the object holder, and several regions of the blade can be successively brought into use in this manner. This of course has the consequence that the knife holder has a large width, which is not ergonomic. In particular, the removal of the sections with the finger is hindered by the great width of the knife holder, and the person operating the equipment has no way of monitoring which regions of the knife have already been used and which are still sharp. The danger of accidents is also increased by the length of the knife. A finger protector can counter this, but this makes it awkward to work with the equipment. Also, when different regions of the blade are successively used, the blade is then used up relatively quickly and must be changed.

SUMMARY OF THE INVENTION

The invention has as its object to construct a knife holder and a knife of the above-mentioned kind, such that the knife holder can be constituted to be ergonomic, work is simpler and safer, and also the knife does not have to be changed so often.

In terms of the knife holder, this object is attained in that the knife receiver is constituted for the reception of a disk-shaped knife which has the shape of a regular polygon, the edges of which are cutting edges, wherein the knife receiver has a shaft by which the knife is rotatable so that the cutting edges can be positioned to cut an object.

In terms of the knife, the object is attained in that it is constituted in a disk form in the form of a regular polygon, wherein the edges are cutting edges.

Due to the shape of the knife as a polygon, the knife holder can be constituted to be relatively narrow and hence also ergonomic. Such a polygon has as many cutting edges as it has edges; for example, in a preferred octagonal form, eight cutting edges are available. Although the individual cutting edges are shorter than the knives mentioned at the beginning, which reduces the danger of accidents and makes a covering with a finger protector superfluous, the total length of cutting edges of the knife according to the invention is considerably larger than that of the knives mentioned at the beginning. Due to the rotation of the knife, better account can be kept of which portions are already used and which are still sharp. In order to facilitate this, a preferred embodiment provides a numbering associated with the cutting edges of a knife. Since the knife according to the invention is clamped in its surface—and thus not laterally—nearly a hundred percent of its cutting edges can be made use of.

In a particularly suitable embodiment, the knife holder has a depression, and an opening serves for the working use of one of the cutting edges, and this cutting edge projects beyond this opening far enough that a cut can be made with it. The depression serves to receive the knife and for the protection of the cutting edges which are not in use, thus considerably reducing the danger of accidents.

The knife receiver of the knife holder can be arranged in various ways. A depression of circular contour milled into it is provided in which the knife can turn with little play, and a clamping device serves to arrest the knife for a cut to be performed. The knife receiver will suitably be equipped, however, with a rotatable mounting for the knife.

In an advantageous embodiment, the rotatable mounting has a positioning element for the knife, by which the cutting edges of a knife are mounted in a defined position. Such a positioning element can be arranged as a pin situated outside the middle and engaging in a bore of the knife, as a projection affixed to the shaft on which the knife is placed, or in other ways.

Work is greatly facilitated by the knife holder having a detent for the rotatable mounting, latching when a cutting edge is situated in its cutting position. The knife is thus in the correct cutting position after each further rotation, and no adjustment is necessary. The detent can be constituted in an optional manner.

The rotatable mounting can be arranged in a manner such that the knife is clamped between two surfaces of the same, or it is possible for the knife receiver to have a plane surface arranged such that the knife can be positioned between this and the rotatable mounting. The plane surface and the shaft can then be situated on the knife holder housing, or it is possible for the shaft to be a portion of the mounting which is inserted into a bore of the plane surface and anchored there. In the first case, the knife is first placed on the shaft, and the rotatable mounting is fastened to the shaft. In the second case, the knife is placed on the shaft of the rotatable mounting, and the shaft is then inserted into the knife holder housing, so that the shaft and/or the mounting is held rotatably or else arrestably. In both cases, or also for other embodiments, it is possible for a releasable stop for the rotation of the knife to be provided, to fix the knife in the cutting positions.

The nearly round shape of the knife makes it possible to constitute the knife holder housing in a particularly ergonomic manner. The space required for a cutting edge is thus relatively small, and it is possible for the knife holder housing to be beveled or rounded, left and right of the mounting for the cutting edge which is ready for use.

The knife is also constituted corresponding to the constitution of the knife holder. It can be a simple polygon that can be placed in a milled-out recess that is shaped in a round shape or in the same polygonal shape as the knife. It can have a square or hexagonal hole in the middle for a corresponding shaft, or a bore for placing on a round shaft. In the latter case, it is suitable for the knife to have a contact for a positioning element of the knife receiver, correspondingly, as described above, as a bore, a notch for the engagement of a lug, or in another manner.

BRIEF DESCRIPTION OF THE DRAWINGS

The invention will be explained hereinbelow with reference to a possible embodiment example, and further possibilities of configuration will be mentioned.

DETAILED DESCRIPTION OF PREFERRED EMBODIMENTS

Figure 1:
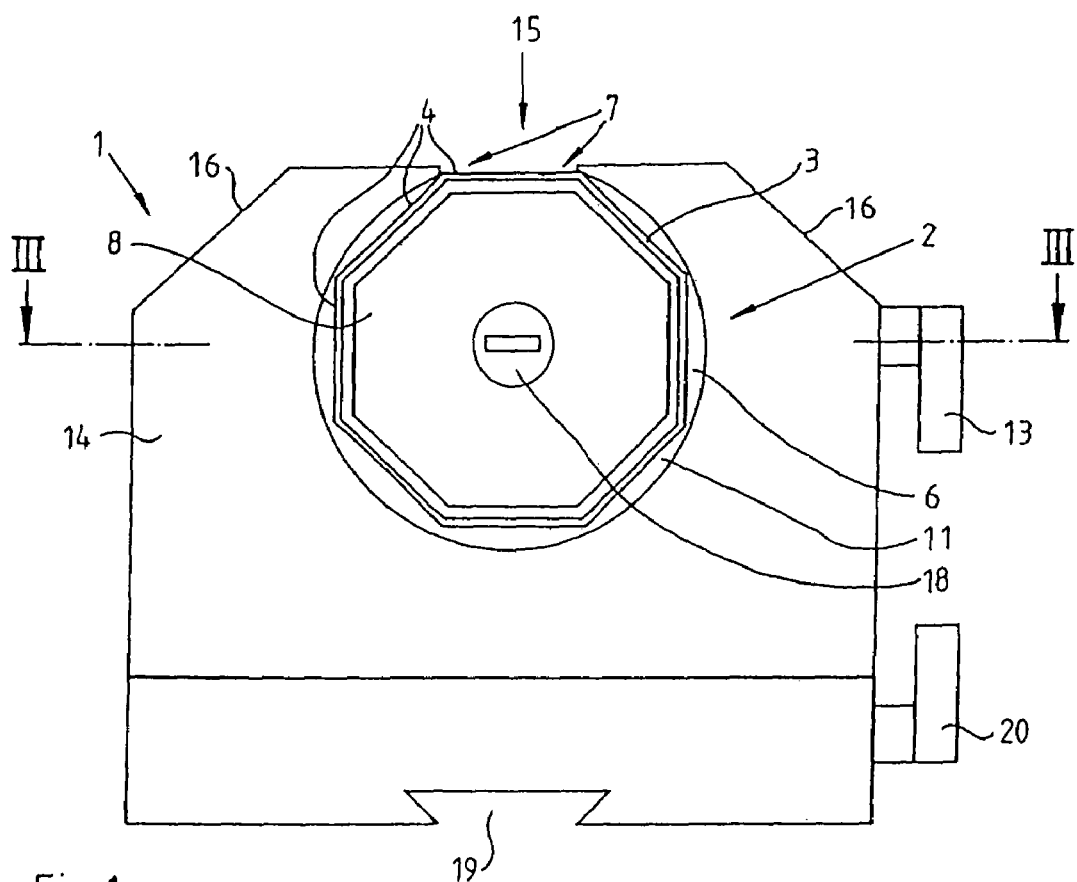
FIG. 1 shows an embodiment of the invention in front view.

FIG. 1 shows a knife holder 1 with a knife receiver 2, in which a knife 3 having the form of an octagon is mounted. The knife 3 has eight cutting edges 4, one of which is situated in the location 15 for working use. The knife 3 is held by a rotatable mounting 8 in which it is inserted, between this and a plane surface 11 of the knife holder housing 14. A positioning element 9 (FIG. 3) insures that the knife 3 assumes a defined position to the rotatable mounting 8. By the rotation of the mounting 8, each optional cutting edge 4 of the knife 3 can be brought to the location 15. For working use, the knife 3 is clamped by means of a stop 13. In order for the cutting edges 4 which are not in working use to be protected, the knife 3 is situated in a depression 6 of the knife holder housing 14, the floor of which forms the plane surface 11. Only the cutting edge 4 designated for working use is situated at an opening 7 of the depression 6 at the upper edge of the knife holder housing 14, so that this cutting edge 4 projects outward and is ready for a cut.

For changing the knife 3, the stop 13 is released, the closure 18 is opened, and the rotatable mounting 8 is taken out together with the knife 3. For easy working, it is appropriate to make the mounting 8 of magnetic material so that the knife 3 adheres to it. The closure 18 can be made with a threaded closure, bayonet closure, or other quickly releasable connection. A guide 19 serves for the attachment of the knife holder 1 to the microtome, and the stop 20 for fixing in the desired position. The knife holder housing 14 can be ergonomically arranged with chamfers 16 or by rounding off.

Figure 2:
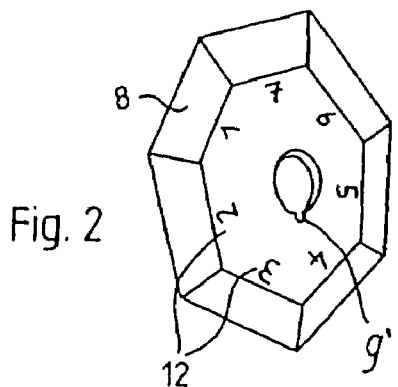
FIG. 2 shows a rotatable mounting.

FIG. 2 shows the rotatable mounting 8 arranged with a numbering 12 whereby it can be better determined which cutting edge 4 of the knife 3 has already been used and which is still sharp. A notch 9' is on the hole through the center of the rotatable mounting 8. The lug 9 passes through the notch 9'.

Figure 3:
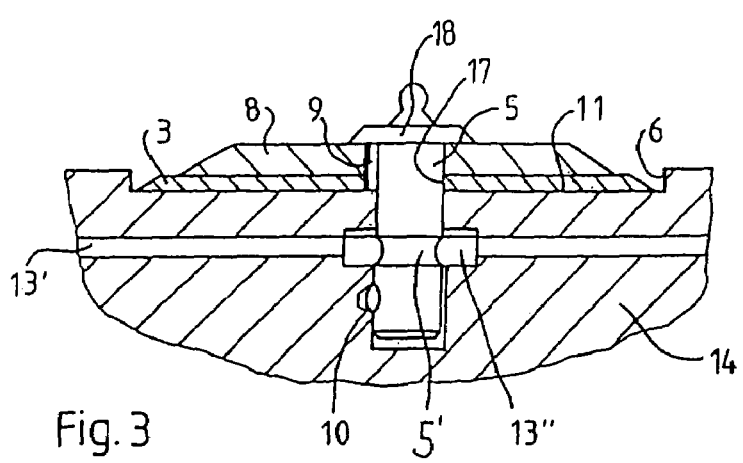
FIG. 3 shows a partial view in the section III—III.

FIG. 3 shows a partial view in the form of a section III—III of FIG. 1. The arrangement of the knife 3 in the knife holder housing 14 is shown. The knife 3 is placed with the mounting 8 on shaft 5 and is held by means of a closure 18. The positioning element, constituted as a lug 9 on the shaft 5 and as notches 9' on the mounting 8 and knife 3 serves to determine the position of the cutting edges 4 with respect to the shaft 5 and thus with respect to a detent 10.

The detent 10, constituted as a spring-loaded ball or in another manner, engages in latching positions such that the cutting edges 4 always arrive in the correct working position upon rotation of the mounting 8 with the knife 3. For the use of a cutting edge 4, the knife 3 and the mounting 8 is fixed by means of a fixing device 13. For this purpose, in this embodiment, a shaft 5' with an eccentric 13" is proposed, wherein the latter engages in a groove 5' of the shaft 5. By the actuation of the lever of the fixing device 13, the mounting 8 with the knife 3 can be fixed, or can be released for turning further on or for changing the knife 3.

In the knife holder according to the invention, the rotation axis of the rotatable mounting 8, i.e., the rotation axis of the shaft 5', is perpendicular to the plane surface 11 of the knife holder and hence perpendicular to the plane of the cutting edges 4 of the knife 3 to be received in the knife holder. In addition to this rotation axis for the knife 3, the knife holder can have a further clampable rotation axis for setting the free angle between the plane of the knife 3 to be received and the specimen to be cut; such a rotation axis is then situated parallel to the plane surface 11 of the knife holder housing 14; preferably, such a rotation axis coincides with the cutting edge 4, more precisely, with the cutting edge, located in the working position, of the knife. The technical realization of such a rotation axis for free angle location is known from the state of the art, for example, in that the knife holder housing 14 is divided between the receiver for the knife 3 and the guide 19 along a partial portion of a cylindrical envelope whose cylinder axis coincides with the cutting edge of the knife to be received; it therefore needs no further description here.

Furthermore, the knife does not need to be constituted in one piece for the knife holder according to the invention. It is also conceivable that the knife is a combination of several parts, e.g., the knife consists of a polygonal blade holder, in which a corresponding number of blades is received along the peripheral edges.

The embodiment shown is solely as an example. As already stated hereinabove, numerous other embodiments are conceivable, in particular for the location and the changing of the knife 3, and also for the construction of the stop and the embodiment of the detent.

I claim:

1. In a microtome for the production of tissue sections in histology, in which an object to be sectioned is passed past a stationary knife for production of the tissue sections, the improvement comprising:

the stationary knife comprising a disk-shaped knife, which has the shape of a regular polygon, having a perimeter with edges that comprise cutting edges, and a knife holder with a knife receiver for arresting and positioning said disk-shaped knife, wherein said knife is received in said knife receiver, wherein said knife receiver has a shaft about which said knife is rotatable and, whereby by rotation of said knife about said shaft, said knife is moved into cutting positions wherein various ones of said cutting edges are brought into a working location to cut said object, and wherein said knife receiver further has a depression in which said knife is received and for protection of said cutting edges, with an opening at said working location that exposes only a selected one of said cutting edges and serves for working use of said selected one of said cutting edges, wherein the perimeter of said knife is completely surrounded by a wall of said depression except at said working location.

2. The microtome according to claim 1, wherein said knife receiver comprises a rotatable mounting that mounts said knife in said knife receiver.

3. The microtome according to claim 2, wherein said rotatable mounting has a positioning element for holding said knife in position, by which positioning element said cutting edges of said knife come into a defined position relative to said mounting.

4. The microtome according to claim 3, wherein said knife holder has a detent for said shaft that latches said rotatable mounting when one of said cutting edges is situated in a cutting position.

5. The microtome according to claim 2, wherein said knife receiver has a plane surface wherein the knife is positioned between said plane surface and said rotatable mounting.

6. The microtome according to claim 1, further comprising a numbering arrangement assigned to said cutting edges of said knife.

7. The microtome according to claim 1, further comprising a releasable stop for fixing said knife in one of said cutting positions.

8. The microtome according to claim 1, wherein said knife holder comprises a knife holder housing that is chamfered left and right of said working location for said cutting edge when said cutting edge is in a position for use.

9. The microtome according to claim 1, wherein said knife has a bore in its middle for reception of said knife in said knife receiver.

10. The microtome according to claim 1, wherein said knife has an engagement element that cooperates with a positioning element of said knife receiver.

11. The microtome according to claim 1, wherein said knife comprises an octagon shape.

\* \* \* \* \*